United States Patent
Porter et al.

(10) Patent No.: US 7,858,388 B2
(45) Date of Patent: Dec. 28, 2010

(54) MS BASED PEPTIDE AND PROTEIN SEQUENCING VIA REACTIONS OF LYSINE RESIDUES WITH PEROXYCARBONATE COMPOUNDS

(75) Inventors: Ned A. Porter, Franklin, TN (US); Douglas S. Masterson, Petal, MS (US); Huiyong Yin, Brentwood, TN (US); Richard M. Caprioli, Brentwood, TN (US); Jeremy L. Norris, Knoxville, TN (US)

(73) Assignee: Vanderbilt University, Nashville, TN (US)

( * ) Notice: Subject to any disclaimer, the term of this patent is extended or adjusted under 35 U.S.C. 154(b) by 844 days.

(21) Appl. No.: 10/576,218

(22) PCT Filed: Oct. 14, 2004

(86) PCT No.: PCT/US2004/033951

§ 371 (c)(1),
(2), (4) Date: Jul. 5, 2007

(87) PCT Pub. No.: WO2005/037857

PCT Pub. Date: Apr. 28, 2005

(65) Prior Publication Data

US 2007/0249056 A1   Oct. 25, 2007

(51) Int. Cl.
*G01N 24/00* (2006.01)
*G01N 33/00* (2006.01)

(52) U.S. Cl. .......................... 436/173; 436/86; 436/87; 436/88; 436/89

(58) Field of Classification Search ........................ None
See application file for complete search history.

(56) References Cited

PUBLICATIONS

Richardson et al. "Equilibria, Kinetics, and Mechanism in the Bicarbonate Activation of Hydrogen Peroxide: Oxidation of Sulfides by Peroxymonocarbonate", J. Am. Chem. Soc. 2000, vol. 122, pp. 1729-1739.*
Masterson et al. "Lysine Peroxycarbamates: Free Radical-Promoted Peptide Cleavage", J. Am. Chem. Soc. 2004, vol. 126, pp. 720-721 (pubished on-line Dec. 31, 2003.*
Aebersold, R.; Goodlett, D. R. Chem. Rev. 2001, 101, 269-295.
Bonetto, V.; Bergman, A.; Joernvall, H.; Sillard, R. Anal. Chem. 1997, 69, 1315-1319.
Bourgeois, M. J.; Campagnole, M.; Filliatre, C.; Maillard, B.; Manigand, C.; Villenave, J. J. Tetrahedron 1982, 38, 3569-3577.
Glocker, M. O.; Borchers, C.; Fieldler, A.; Suckau, D.; Przybylski, M. Bioconjugate Chem. 1994, 5, 583-590.
Griep-Raming, J.; Meyer, S.; Bruhn, T.; Metzger, J. O. Angew. Chem. Int. Ed. Engl. 2002, 41, 2738-2742.
Hawkins, C, L.; Davies, M. J. Biochem. Biophys. Acta. 2001, 1504, 196-219.
Julian, R. R.; May, J. A.; Stoltz, B. M.; Beauchamp, J. L. Angew. Chem. Int. Ed. Engl. 2003, 42, 1012-1015.
Kelleher, N. L.; Lin, H. Y.; Valaskovic, G. A.; Aaserud, D. J.; Fridriksson, E. K.; McLafferty, F. W. J. Am. Chem. Soc. 1999, 121, 806.
Majetich, G.; Wheless, K. Tetrahedron 1995, 51, 7095-7129.
McLuckey, S. A.; Reid, G. E. J. Mass. Spectrom. 2002, 37, 663-675.
Yates, J. R. J. Mass. Spectrom. 1998, 33, 1-19.
Yin, H.; Hachey, D. L.; Porter, N. A. J. Am. Soc. Mass Spectrom. 2001, 12, 449-455.

* cited by examiner

*Primary Examiner*—Yelena G Gakh
(74) *Attorney, Agent, or Firm*—Stites & Harbison PLLC; Richard S. Myers, Jr.

(57) ABSTRACT

A method of modifying protein samples that comprises combining the sample with a peroxycarbonate solution and inserting the sample into a mass spectrometer. The present invention also includes methods of N-terminus characterization.

9 Claims, 3 Drawing Sheets

MS BASED PEPTIDE AND PROTEIN SEQUENCING VIA REACTIONS OF LYSINE RESIDUES WITH PEROXYCARBONATE COMPOUNDS

TECHNICAL FIELD OF THE INVENTION

The present invention relates to the field of proteomics and analytical methods used in the determination of protein structures. More particularly, the present invention provides a process for modifying peptides and proteins on lysine amino groups such that the modification leads to fragmentation at or near the lysine position in a mass spectrometer.

Additionally, the present invention relates to methods of modifying amino acids and peptides. More particularly, embodiments of this method modify amino acids and peptides to form a t-butyl-peroxycarbamate compound. This aspect of the present invention is useful for the development of N-terminus characterization methods.

BACKGROUND OF THE INVENTION

A popular method for sequencing proteins (such as, for example, in proteomics applications) involves enzymatic digestion (trypsin, chymotrypsin, etc.) of a large protein into smaller peptides and subsequent MS sequencing of the smaller peptides.

In view of the difficulties of the prior art process, what is needed is a method that provides for the convenient and rapid quantification of proteins. The present invention provides such a method.

The present invention may be used in place of the enzymatic digestion process, and embodiments of the present invention lead to high-throughput strategies that involve predictable fragmentation of proteins in a mass spectrometer into smaller pieces that can be ultimately sequenced quickly and easily.

SUMMARY OF THE INVENTION

As stated above, the prior art process of separating and identifying proteins that includes enzymatic digestion is a difficult and time-intensive process. Thus, an aspect of the present invention is to provide protocols that lead to fragmentation of large proteins in a predictable way. In embodiments of the present invention, the fragmentation takes place in a mass spectrometer inlet or in a mass spectrometer collision cell.

Another aspect of the present invention is to provide a high throughout procedure for the quantification of proteins.

Another aspect of the present invention is to provide a convenient and rapid method to quantify proteins.

Another aspect of the present invention is to provide a predictable peptide fragmentation in a mass spectrometer at or near the modified lysine residues of small peptides.

Another aspect of the present invention is to provide novel peroxycarbonate compounds.

Another aspect of the present invention is to provide a method of chemically modifying peptides by modifying the N-terminal amino group.

Finally, another aspect of the present invention is to provide novel peroxycarbonate/lysine (or lysine residue) combinations, and to provide novel peroxycarbonate/protein (or protein residue) as well as novel peroxycarbonate/peptide (or peptide residue) combinations.

Of course, the above named aspects of the present invention are not exclusive and should not be construed as limiting of the present invention. Other aspects will become readily apparent upon a reading of this Specification and claims.

One embodiment of the present invention is a method of identifying protein sequences that comprises providing a protein sample, providing a peroxycarbonate solution, combining the protein sample and the peroxycarbonate sample to form a sample solution, inserting the sample solution into a mass spectrometer, and analyzing the mass spectrometer results using standard mass spectrometer procedures. In other embodiments there is an incubation step after the combining step. This incubation step may comprise incubating the sample solution at room temperature for a period of time such as for up to about 1-3 hours.

The method of the present invention may be performed using any mass spectrometry system. In embodiments of the present invention, the mass spectrometer is a Matrix Assisted Laser Desorption Ionization (MALDI) mass spectrometer. Other embodiments include the use of such systems as electrospray ionization (ESI), electron impact (EI), chemical ionization (CI), fast atom bombardment (FAB), Fourier Transform Ion Cyclotron Resonance (FTICR), etc. Embodiments of the present invention include collision-induced dissociation (CID) mass spectrometry and ion trap equipped mass spectrometry as well.

DESCRIPTION OF THE INVENTION

Figure 1:
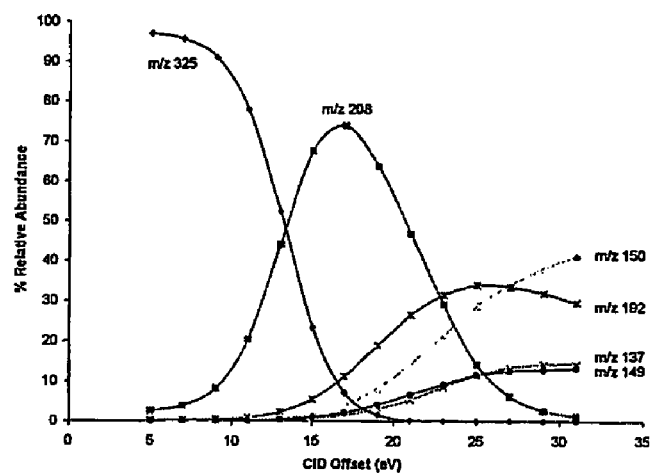
FIG. 1 is a chart showing electrospray collision induced ions formed from lithium complex of the peroxycarbamate (Ac-LPC-OMe) vs. offset energy.

Digestion by protease enzymes is an important part of the standard protocol used to provide protein primary structural information. Large proteins are converted in a predictable way to smaller peptide fragments that can be readily identified. Thus, the cornerstone methods used in protein identification are enzymatic proteolysis, separations such as chromatography and electrophoresis, and analysis of isolated small peptide fragments by mass spectrometry.

Chemical digestion of proteins has also provided strategies that are helpful in assignment of peptide sequences. Both chemical and enzymatic protein digestion, however, can be cumbersome and time-consuming and attempts to avoid this step by the use of powerful mass spectrometric "top-down" approaches are being explored to provide protein primary sequences.

Strategies that combine in one step a predictable chemical-based protein digestion with mass spectrometry might prove to be convenient for rapid primary peptide sequence analysis. Toward this end, the present inventors have discovered chemical procedures for gas phase peptide fragmentation that is appropriate for use in mass spectrometry.

As indicated above, an aspect of the present invention is a method of identifying protein sequences that comprise providing a sample and a peroxycarbonate solution. In that and other aspects of the present invention, the peroxycarbonate solution of the present invention may comprise the following compound:

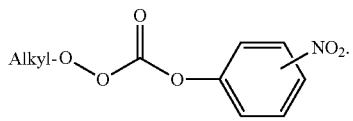

"Alkyl," as used herein, is to be understood in the broadest sense to mean hydrocarbon residues which can be linear, i.e., straight-chain, or branched, and can be acyclic or cyclic residues or comprise any combination of acyclic and cyclic subunits. Further, the term alkyl as used herein expressly includes saturated groups as well as unsaturated groups which latter groups contain one or more, for example, one, two, or three, double bonds and/or triple bonds.

All these statements also apply if an alkyl group carries substituents or occurs as a substituent on another residue, for example, in an alkyloxy residue, or an arylallkylamino residue. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl, and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl, or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl residues such as ethynyl, 1-propynyl, 2-propynyl (=propargyl), or 2-butynyl. Alkyl residues can also be unsaturated when they are substituted.

Examples of cyclic alkyl residues are cycloalkyl residues containing 3, 4, 5, 6, 7, or 8 ring carbon atoms like cyclopropyl, cyclobutyl, cyclopentyl, cyclohexyl, cycloheptyl, or cyclooctyl which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloallkyl-substituted alkyl groups like cyclopropylmethyl-, cyclobutylmethyl-, cyclopentylmethyl-, cyclohexylmethyl-, cycloheptylmethyl-, cyclooctylmethyl-, 1-cyclopropylethyl-, 1-cyclobutylethyl-, 1-cyclopentylethyl-, 1-cyclohexylethyl-, 1-cycloheptylethyl-, 1-cyclooctylethyl-, 2-cyclopropylethyl-, 2-cyclobutylethyl-, 2-cyclopentylethyl-, 2-cyclohexylethyl-, 2-cycloheptylethyl-, 2-cyclooctylethyl-, 3-cyclopropylpropyl-, 3-cyclobutylpropyl-, 3-cyclopentylpropyl-, 3-cyclohexylpropyl-, 3-cycloheptylpropyl-, or 3-cyclooctylpropyl- in which groups the cycloalkyl subgroup as well as acyclic subgroup also can be unsaturated and/or substituted.

Of course, a group like ($C_1$-$C_8$)-alkyl is to be understood as comprising, among others, saturated acyclic ($C_1$-$C_8$)-alkyl, ($C_3$-$C_8$)-cycloalkyl, cycloalkyl-alkyl groups like ($C_3$-$C_7$)-cycloalkyl-($C_1$-$C_5$)-alkyl- wherein the total number of carbon atoms can range from 4 to 8, and unsaturated ($C_2$-$C_8$)-alkyl like ($C_2$-$C_8$)-alkenyl or ($C_2$-$C_8$)-alkynyl. Similarly, a group like ($C_1$-$C_4$)-alkyl is to be understood as comprising, among others, saturated acyclic ($C_1$-$C_4$)-alkyl, ($C_3$-$C_4$)-cycloalkyl, cyclopropyl-methyl-, and unsaturated ($C_2$-$C_4$)-alkyl like ($C_2$-$C_4$)-alkenyl or ($C_2$-$C_4$)-alkynyl.

Unless stated otherwise, the term alkyl preferably comprises acyclic saturated hydrocarbon residues containing from 1 to 6 carbon atoms which can be linear or branched, acyclic unsaturated hydrocarbon residues containing from 2 to 6 carbon atoms which can be linear or branched like ($C_2$-$C_6$)-alkenyl and ($C_2$-$C_6$)-alkynyl, and cyclic alkyl groups containing from 3 to 8 ring carbon atoms, in particular from 3 to 6 ring carbon atoms. A particular group of saturated acyclic alkyl residues is formed by ($C_1$-$C_4$)-alkyl residues like methyl, ethyl, n-propyl, isopropyl, n-butyl, isobutyl, sec-butyl, and tert-butyl.

The alkyl groups of the present invention can in general be unsubstituted or substituted by one or more, for example, one, two, three, or four, identical or different substituents. Any kind of substituents present in substituted alkyl residues can be present in any desired position provided that the substitution does not lead to an unstable molecule. Examples of substituted alkyl residues are alkyl residues in which one or more, for example, 1, 2, 3, 4, or 5, hydrogen atoms are replaced with halogen atoms.

Examples of substituted cycloalkyl groups are cycloalkyl groups which carry as substituent one or more, for example, one, two, three, or four, identical or different acyclic alkyl groups, for example, acyclic ($C_1$-$C_4$)-alkyl groups like methyl groups. Examples of substituted cycloalkyl groups are 4-methylcyclohexyl, 4-tert-butylcyclohexyl, or 2,3-dimethylcyclopentyl.

The term aryl refers to a monocyclic or polycyclic hydrocarbon residue in which at least one carbocyclic ring is present. In a ($C_6$-$C_{14}$)-aryl residue from 6 to 14 ring carbon atoms are present. Examples of ($C_6$-$C_{14}$)-aryl residues are phenyl, naphthyl, biphenylyl, fluorenyl, or anthracenyl. Examples of ($C_6$-$C_{10}$)-aryl residues are phenyl or naphthyl. Unless stated otherwise, and irrespective of any specific substituents bonded to aryl groups, aryl residues including, for example, phenyl, naphthyl, and fluorenyl, can in general be unsubstituted or substituted by one or more, for example, one, two, three, or four, identical or different substituents. Aryl residues can be bonded via any desired position, and in substituted aryl residues the substituents can be located in any desired position.

In monosubstituted phenyl residues, the substituent can be located in the 2-position, the 3-position, or the 4-position, the 3-position and the 4-position being preferred. If a phenyl group carries two substituents, they can be located in 2,3-position, 2,4-position, 2,5-position, 2,6-position, 3,4-position, or 3,5-position. In phenyl residues carrying three substituents, the substituents can be located in 2,3,4-position, 2,3,5-position, 2,3,6-position, 2,4,5-position, 2,4,6-position, or 3,4,5-position. Naphthyl residues can be 1-naphthyl and 2-naphthyl. In substituted naphthyl residues, the substituents can be located in any positions, for example, in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position. Biphenylyl residues can be 2-biphenylyl, 3-biphenylyl, or 4-biphenylyl. Fluorenyl residues can be 1-, 2-, 3-, 4-, or 9 -fluorenyl. In monosubstituted fluorenyl residues, bonded via the 9-position the substituent is preferably present in the 1-, 2-, 3-, or 4-position.

Unless stated otherwise, substituents that can be present in substituted aryl groups are, for example, ($C_1$-$C_8$)-alkyl, in particular ($C_1$-$C_4$)-alkyl, such as methyl, ethyl, or tert-butyl, hydroxy, ($C_1$-$C_8$)-alkyloxy, in particular ($C_1$-$C_4$)-alkyloxy, such as methoxy, ethoxy, or tert-butoxy, methylenedioxy, ethylenedioxy, F, Cl, Br, I, cyano, nitro, trifluoromethyl, trifluoromethoxy, hydroxymethyl, formyl, acetyl, amino, mono- or di-($C_1$-$C_4$)-alkylamino, (($C_1$-$C_4$)-alkyl)carbonylamino like acetylamino, hydroxycarbonyl, ((C₁-C₄)-alkyloxy) carbonyl, carbamoyl, optionally substituted phenyl, benzyl optionally substituted in the phenyl group, optionally substituted phenoxy, or benzyloxy optionally substituted in the phenyl group.

The above statements relating to aryl groups correspondingly apply to divalent residues derived from aryl groups, i.e., to arylene groups like phenylene which can be unsubstituted or substituted 1,2-phenylene, 1,3-phenylene, or 1,4-phenylene, or naphthalene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl, or 2,7-naphthalenediyl.

The above statements also correspondingly apply to the aryl subgroup in arylalkyl-groups. Examples of arylalkyl-groups which can also be unsubstituted or substituted in the aryl subgroup as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, or 9-fluorenylmethyl.

Alkoxy as used herein means an alkyl-O— group in which the alkyl group is as previously described. Exemplary alkoxy groups include methoxy, ethoxy, n-propoxy, i-propoxy, n-butoxy, t-butoxy and polyethers including —O—(CH₂)₂OCH₃.

An acyl group is defined as a group —C(O)R where R is an alkyl or aryl radical and includes acetyl, trifluoroacetyl, benzoyl and the like.

Where terms are used in combination, the definition for each individual part of the combination applies unless defined otherwise. For instance, arylalkylthio refers to an aryl group, as defined above, alkyl group as defined above, and a thio group. An example is alkylamino, which is defined as a nitrogen atom substituted with an alkyl of 1 to 12 carbon atoms. Also, thioalkyl, or alkylthio as used herein means an alkyl-S— group in which the alkyl group is as previously described. Thioalkyl groups include thiomethyl and the like. Examples of alkylthio groups of compounds of the present invention includes those groups having one or more thioether linkages and from 1 to about 12 carbon atoms, further examples have from 1 to about 8 carbon atoms, and still further examples have 1 to about 6 carbon atoms. Alkylthio groups having 1, 2, 3 or 4 carbon atoms are further examples.

Some of the compounds of the invention may have stereogenic centers. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. Thus, when using the term compound, it is understood that all stereoisomers are included.

In embodiments of the present invention, "alkyl" may specifically include carbon fragments having up to 20 carbon atoms. Examples of alkyl groups include butyl, octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like. In one embodiment, "alkyl" is t-butyl.

In embodiments of the present invention, the peroxycarbonate solution comprises at least one of the following compounds:

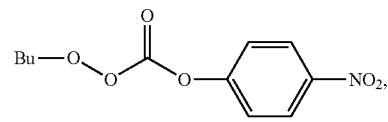

wherein "Bu" includes t-butyl;

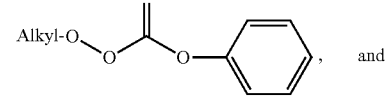

and

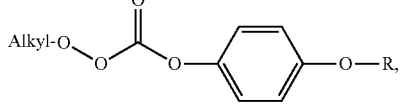

wherein alkyl is the same as the definition above, and R is a substituent, including alkyl.

When used herein, the term "substituent" includes those listed in the definition of alkyl. Additionally, "ubstituents" can independently be hydrogen, alkyl (substituted or unsubstituted, as defined herein), carbonyl.

In other embodiments of the present invention, the peroxycarbonate of the present invention may comprise at least one of the following compounds:

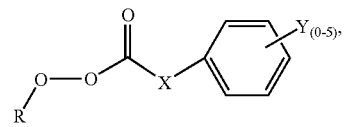

wherein R is an alkyl group (as defined above), X is a leaving group and the phenyl group, and Y is hydrogen or a substituent. Each Y may be the same or different.

In other embodiments, X may be O, S, or NH. Y may be CN, OR, NO₂, CO₂H, CO₂R, halogen (including Cl). As indicated above, there may be 0, or 1-5 independent Y groups present in the compound.

Further, the peroxycarbonate solution of the present invention may comprise at least one of the following compounds:

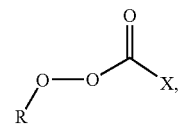

wherein R is alkyl and X is an imidazole group, —OCH₂CF₃,

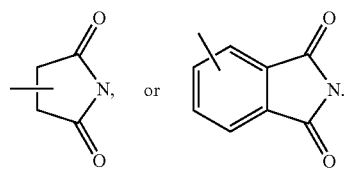

In other embodiments of the present invention, the peroxycarbonate solution of the present invention may comprise at least one of the following compounds:

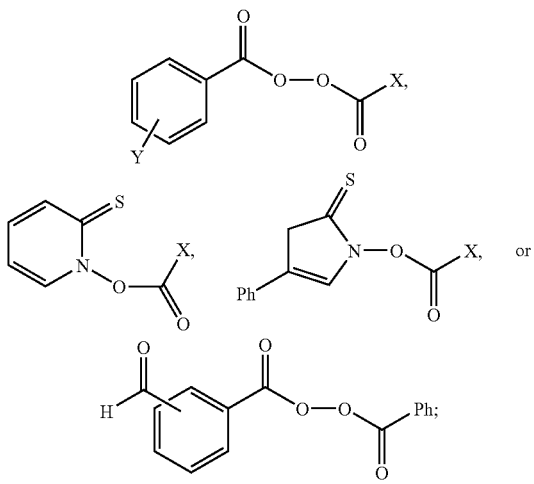

wherein X is any of the X groups defined herein, and Ph can be substituted or unsubstituted.

All peroxycarbonate compounds of the present invention may be isotopically labeled to provide appropriate mass shift within the mass spectrometer. Examples of the labels include D, $O^{18}$, $C^{13}$, $C^{14}$, $H_3$.

The peroxycarbonate solution of the present invention may optionally comprise, in addition to one of the above-described compounds, at least one of a solvent and a buffer. One of ordinary skill in the art can select appropriate buffers and solvents. An example of a solvent is acetonitrile.

A peroxycarbonate compound of the present invention is one of the above compounds and/or one of the above compounds in solution (i.e., compound and solvent).

Other embodiments of the present invention include compounds of the present invention that are a result of a lysine, lysine residue and/or protein, protein fragment and a peroxycarbonate solution. An example includes the following:

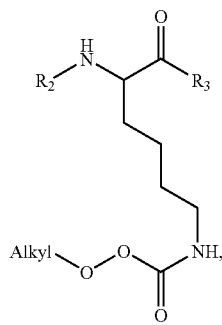

wherein "alkyl" is as defined above; $R_2$ is —CO—CH$_3$ or a peptide; $R_3$ is —NH-peptide or —CO—O—CH$_3$.

The term "peptide" as used herein means a linear compound that consists of two or more amino acids that are linked by means of a peptide bond. The term "peptide" also includes compounds containing both peptide and non-peptide components, such as pseudopeptide or peptidomimetic residues or other non-amino acid components (i.e., a "peptide analog").

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) The Peptides, 5:342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

A method of the present invention includes the steps of providing a protein sample; providing a peroxycarbonate solution; combining the protein sample and the peroxycarbonate solution to form a sample solution; inserting the sample solution into a mass spectrometer; and analyzing the mass spectrometer results using standard mass spectrometry procedures. In other aspects, this method further comprises an incubation step before and/or after the protein sample is combined with the peroxycarbonate. This incubation step can be completed as room temperature.

Embodiments of the present invention also include procedures described below, which are presented for exemplary purposes and to demonstrate the best mode at the time of the invention. As such, this embodiment should not be construed as limiting of the present invention. In this embodiment, lysine residue amino groups in peptides and proteins are modified by reaction with a peroxycarbonate of the present invention 1. Without being bound by theory, the resulting lysine peroxycarbamates undergo homolytic fragmentation under conditions of low energy collision induced dissociation (CID). One result of this process is predictable peptide fragmentation in the mass spectrometer at or near the modified lysine residues of small peptides.

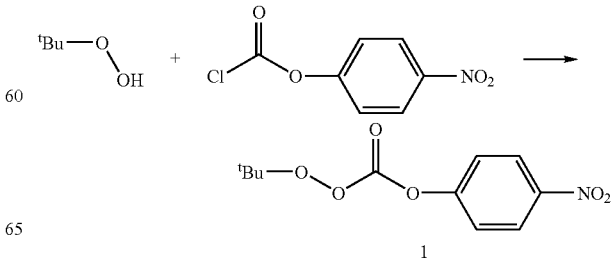

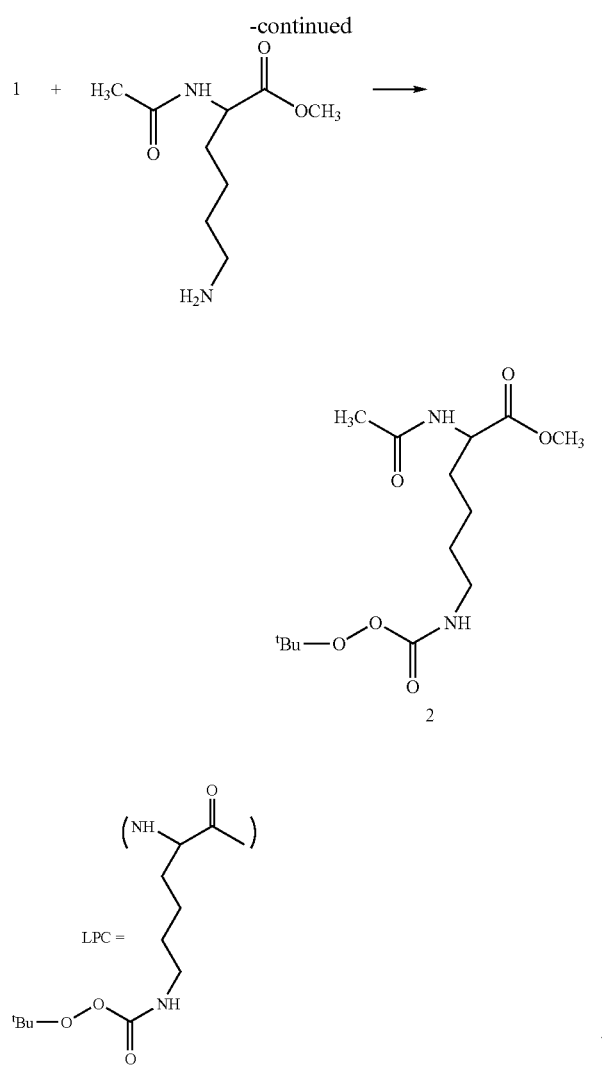

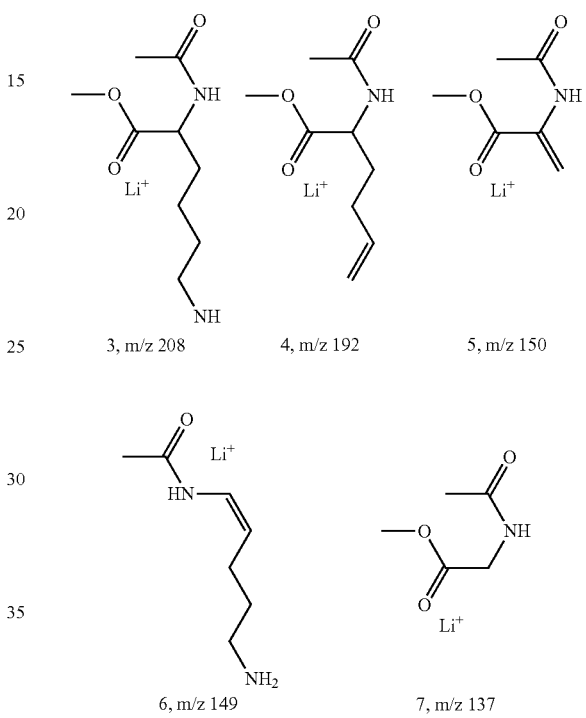

3, m/z 208                4, m/z 192                5, m/z 150

6, m/z 149                7, m/z 137

Reaction of p-nitrophenylchloroformate with tert-butyl hydroperoxide gave the peroxycarbonate 1 which was isolated by silica chromatography as a white solid. Pyridine was added dropwise to a 0° C. methylene chloride solution of the hydroperoxide and chloroformate. The product was characterized by $^1$H and $^{13}$C NMR, HRMS, mp=55-56° C. In basic water or water acetonitrile mixtures, 1 gave an almost immediate yellow color indicative of the formation of p-nitrophenoxide. The half-life of 1 in pH 8.2 phosphate buffer (50% MeOH) is approximately 112 sec. In basic aqueous acetonitrile solutions, αN-acetyl lysine methyl ester was converted cleanly to 2 on reaction with 10 equivalents of 1. The peroxycarbamate 2 (Ac-LPC-OMe) is stable to chromatography and can be fully characterized by spectroscopy and HRMS ("LPC" is used herein for lycine peroxycarbamate).

Analysis of 2 by electrospray shows a parent ion for the H, Li, Na, K, and Ag peroxycarbamate adducts. Collision induced dissociation (CID) of the parent ion led to loss of —C(O)OO$^t$Bu (m/z=117) for each of the adducts. The Li adduct of 2, for example, gave a parent ion at m/z=325, while CID on 2 at −15 eV gave a major ion at m/z=208, see FIG. 1. Increasing CID offset energies gave rise to smaller lithium ion complexes at m/z=192, 149, 150 and 137. CID fragmentation of the lithium adduct of αN-acetyl lysine methyl ester, the precursor to 2, does not give similar ions.

The chemistry associated with the fragmentations of the peroxycarbamate (Li-2, m/z=325) shown in FIG. 1 is consistent with an initial free radical dissociation of the weak —O—O— bond followed by decarboxylation to form an aminyl radical, 3, shown here as the lithium complex. Other adducts formed by subsequent fragmentation of 3 are shown below.

Several peptides were reacted with 1 and adducts or multiple adducts were observed in every case by electrospray mass spectrometry. Thus, Ac-Gly-Ser-Ala-Lys-Val-Ser-Phe (Ac-7; M+1, m/z=853.4) gave a product with 1 at m/z=853.4+116, presumably, Ac-7-LPC Ac-Gly-Ser-Ala-LPC-Val-Ser-Phe. Mass spectral analysis of Ac-7-LPC with added LiCl gave lithium adducts as shown in Scheme 1, E=Li. The formation of each of the species, 9-11 can be understood based upon generation of an intermediate aminyl radical followed by remote hydrogen abstraction and β-fragmentation of the intermediate carbon radical. Of particular interest is the fact that adducts 9 and 11 result from peptide bond fragmentation. The peptide 12, Tyr-Glu-Val-His-His-Gln-Lys-Leu-Val-Phe-Phe gave a peroxycarbamate derivative that also gave peptide cleavage under CID to give a species analogous to 11, as shown in Scheme 1. The conversion of radical 8 to 11 has ample precedent in the well-known Hofmann-Löffler reaction. In this transformation, the protonated aminyl radical 8(E=H$^+$) abstracts a remote H atom via a six-membered ring transition state. The carbon radical formed from this sequence, as shown in Scheme 1, gives 11 by a simple β fragmentation, another reaction that is well-known in radical chemistry.

Scheme 1. Mechanism for Formation of Typical Products formed in Dissociation of LPCs Derived from Peptides.

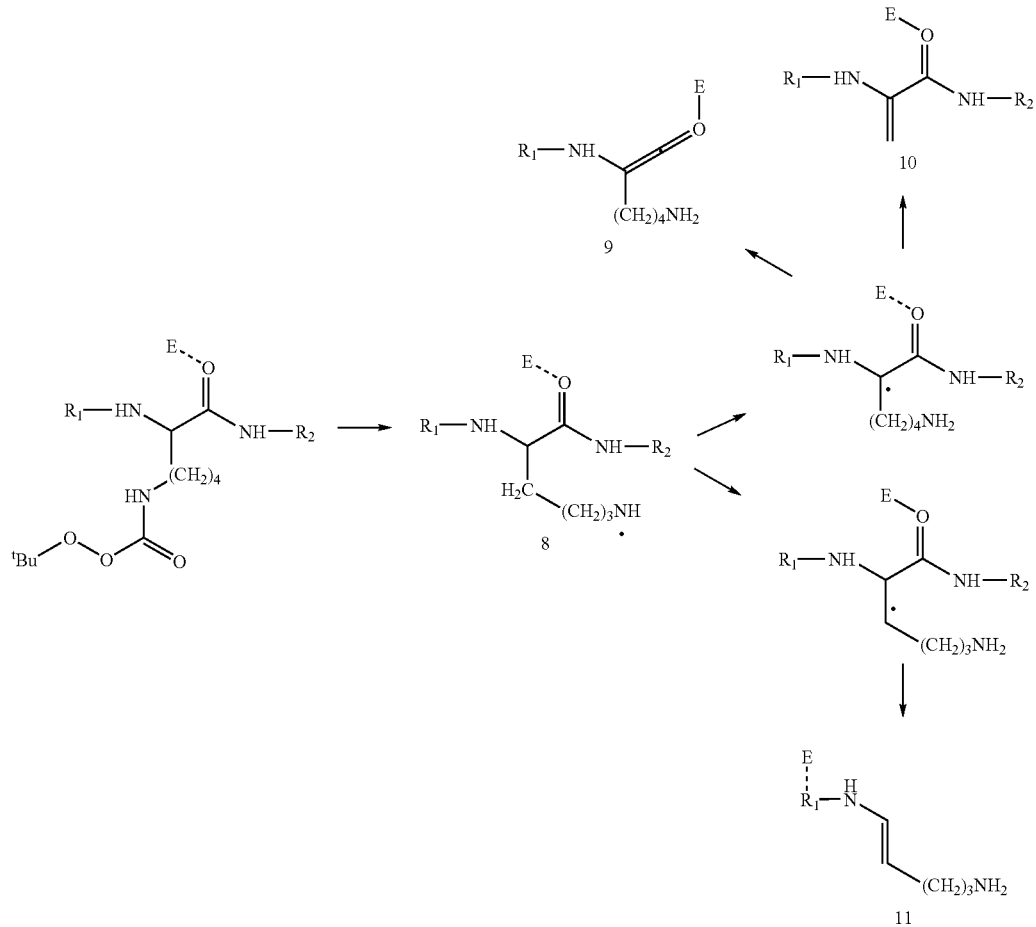

E = H, Li, Na, Ag

Figure 2:
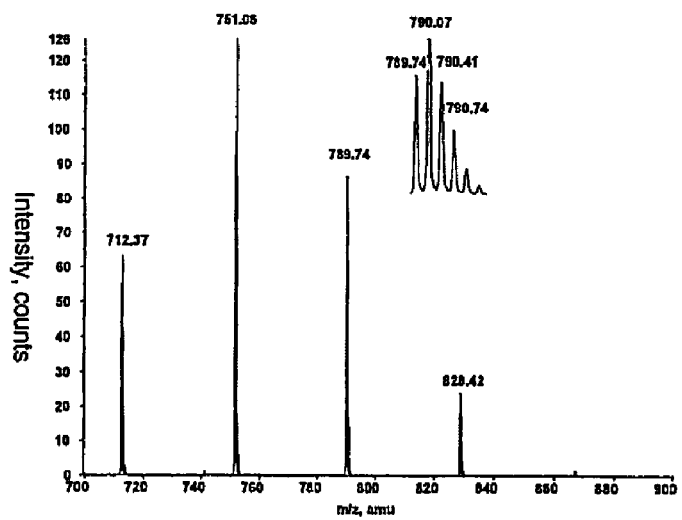
FIG. 2 is an electrospray mass spectrum of peroxy-carbonate modified Ac-13. The inset in FIG. 2 shows an expansion of $(Ac-13-2LPC+3)^{3+}$.

Ac-Ser-Tyr-Ser-Met-Glu-His-Phe-Arg-Trp-Gly-Lys-Pro-Val-Gly-Lys-Lys-Arg (Ac-13, $(M+3)^{3+}$, m/z=712.7) gave products upon reaction with peroxycarbonate 1 in which one, two or three free lysine side chain amino groups were converted to peroxycarbamates. FIG. 2 shows the electrospray mass spectrum for the LPC modified Ac-13. The analogous peptide 13 having a free terminal amine, $NH_2$-Ser-Tyr-Ser-Met-Glu-His-Phe-Arg-Trp-Gly-Lys-Pro-Val-Gly-Lys-Lys-Arg, gave products upon reaction with 1 that had up to four amino groups modified. CID of these modified peptides showed, in every case, loss of n —C(O)OO$^t$Bu, where n is the number of peroxycarbamates in the peptide species analyzed. Thus, dissociation of (Ac-13+LPC+3)$^{3+}$ gave (Ac-13+2)$^{3+}$, presumably the radical species analogous to 8, formed by loss of one peroxycarbamate group while (Ac-13+2LPC+3)$^{3+}$ lost two —C(O)OO$^t$Bu and so forth. Higher offset energies in the CID experiment of the peptides with multiple LPC groups gave complex spectra that were not readily interpretable.

Figure 3:
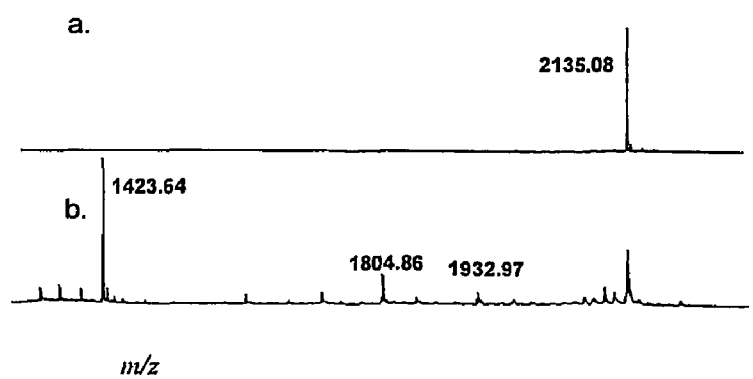
FIG. 3 is a MALDI mass spectrum of (a) Ac-13 and (b) peroxy-carbamate modified Ac-13 consisting of a mixture of compounds 1, 2, and 3 LPC modifications.

Matrix Assisted Laser Desorption Ionization (MALDI) of the percarbamate modified peptides also gave backbone fragments formed by loss of the —C(O)OO$^t$Bu groups. The MALDI experiment for Ac-13 shown in FIG. 3 is typical. The spectrum displayed in FIG. 3b is for the same mixture of LPC modified Ac-13 whose electrospray mass spectrum is shown in FIG. 2. By MALDI, no LPC adducts were observed but a complex set of ions near m/z=2135, that of the parent peptide Ac-13, were observed. The LPC modified peptide clearly did not survive the laser desorption process intact. Fragmentation of the weak peroxide bond presumably leads to aminyl radicals as outlined in Scheme 1. In addition, ions at m/z=1423, 1804 and 1932 were prominent in the LPC modified compound while they were not observed for the parent peptide. Each of these ions corresponds to fragmentation of the peptide at one of the three lysine residues in the peptide, with formation of species analogous the enamide 11 with E=H, as shown in Scheme 1. The ion observed at m/z=1423, for example, corresponds to 11 with E=H and $R_1$=Ac-Ser-Tyr-Ser-Met-Glu-His-Phe-Arg-Trp-Gly while for m/z=1804, $R_1$=Ac-Ser-Tyr-Ser-Met-Glu-His-Phe-Arg-Trp-Gly-Lys-Pro-Val-Gly-and for m/z=1932, $R_1$=Ac-Ser-Tyr-Ser-Met-Glu-His-Phe-Arg-Trp-Gly-Lys-Pro-Val-Gly-Lys. Sequencing experiments on the ion with m/z=1423 are consistent with the proposed structure. Loss of HNC=CH(CH$_2$)$_2$—NH$_2$ from this ion is observed as well as peptide fragmentation expected from the sequence.

A peroxycarbonate 1 preparation of the present invention can be made by charging a 50 ml round bottom flask with 20 about ml of methylene chloride and about 2.0 g (9.9 mMol) of p-nitrophenyl cloroformate. The solution is cooled to about 0° C. and about 1 eq. of t-butyl hydroperoxide in decane is added in one portion. The resulting solution is stirred and 1 eq. of anhydrous pyridine was added dropwise over about 10 minutes. The solution is allowed to ward to room temperature and stirred for an additional hour. About 50 ml of methylene chloride is then added and the solution is washed with about 1% $H_2SO_4$ and washed with brine and then dried over $MgSO_4$. The solution is then concentrated and placed atop a $SiO_2$ column, which was eluted with 1:1 hexane/ether to provide about 1.0 g of pure product as a while solid (about 3.9 mMol, 39%).

Additionally, another aspect of the present invention is a method for directing fragmentation of peptides, comprising providing a peptide and/or a peptide residue; providing a peroxycarbonate solution; and introducing the peptide and/or peptide residue to the peroxycarbonate solution to form a peptide-peroxycarbonate solution. This embodiment is useful as a N-terminus characterization method.

Despite the rapid development of tandem mass spectrometry method for protein sequencing and indentification. "de novo" sequencing strategies continue to be employed for identification of proteins, including identification of novel proteins. In such cases, identification of the N-terminal residues becomes challenging due to the lack of fragmentation at the N-terminal amide bond. One way to overcome this issue is to perform a single Edman degradation cycle to remove the N-terminal residue. Such a strategy is accompanied by the low sensitivity and slow reaction cycles common of Edman degradations: Accordingly, a mass spectrometry based method would provide a fast and efficient solution to this problem.

As discussed herein, the present inventors have discovered that modification of peptides at Lys residues with a peroxicarbonate reagent/solution of the present invention results in peptide peroxycarbonates which undergo free radical promoted fragmentation by collision-induced dissociation. This aspect is related to the loss of the N-terminal side chain, leading to methods of N-terminus characterization of the present invention.

N-terminal side chain loss of derivatized amino acods and peptides is shown by the following scheme:

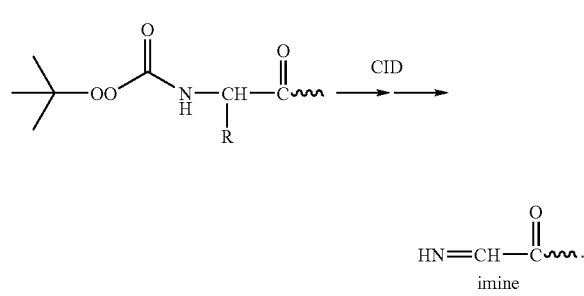

Modification of amino acids and peptides is shown by the following scheme:

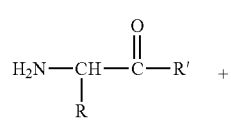

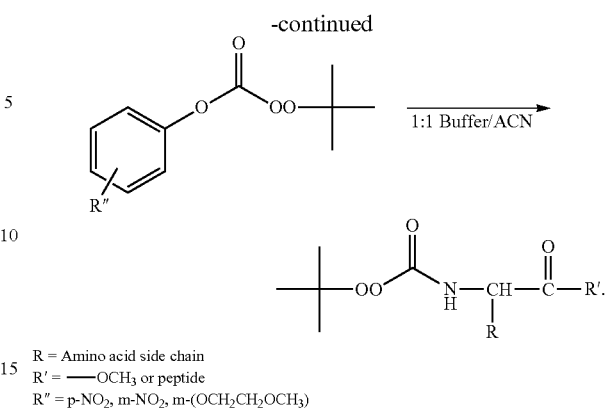

R = Amino acid side chain
R' = ——$OCH_3$ or peptide
R" = p-$NO_2$, m-$NO_2$, m-($OCH_2CH_2OCH_3$)

As an example of this aspect of the present invention is described below. Amino acids are purchased from Aldrich as methyl ester or diethyl ester (as in the case of Asp) hydrochlorides, with the exception of Glu, which is used as the diethyl ester. Modification reactions consists of a mixture of 5 ul of 0.1 M amino acid solution in 1:1 water/acetonitrile (0.01 M final concentration), 20 ul of 1:1 0.1 M $NH_4HCO_3$/ acetronitrile solution, and 20 ul of 0.1M peroxycarbonate reagent solution with R"=p-$NO_2$ (see above) in acetonitrile (0.04 M final concentration). Reactions are incubated at room temperature overnight. Peptides are purchased from American Peptide Company with purity of about >90%. Modification reactions are done on a series of peptides of molecular weights ranging from 700 to 3200 with different N-terminal amino acids (Val, His, Met, ser, Asn, Phe, Lys, Arg, Gly, Trp, Gln, Leu, Tyr and Glu). Reaction conditions vary in pH, reagent used, amount of reagent, and time of incubation to achieve best selectivity for modification of N-terminal over Lys residues. Temperature is kept at 37° C. in all cases. Mass spectrometry analyses are done using a triple quadrupole instrument with an ESI source.

Figure 4:
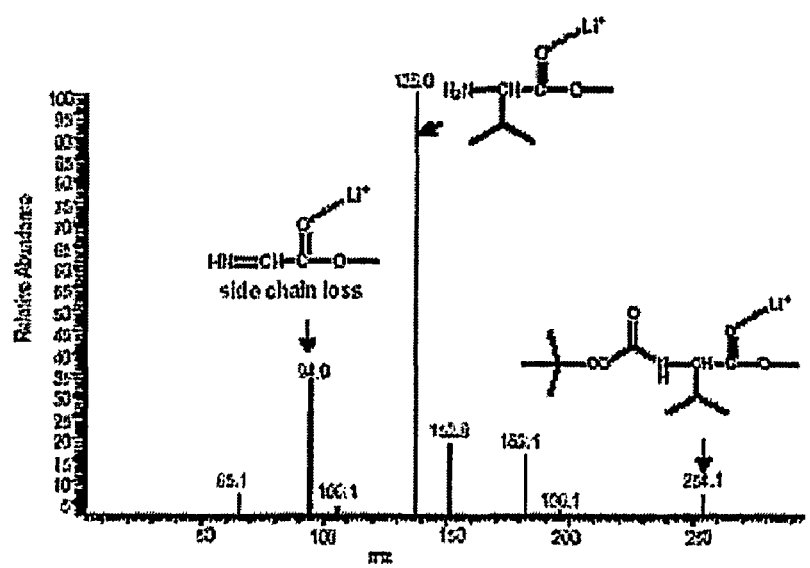
FIG. 4 is an LC/MS graph of a modified peptide of the present invention.
Figure 5:
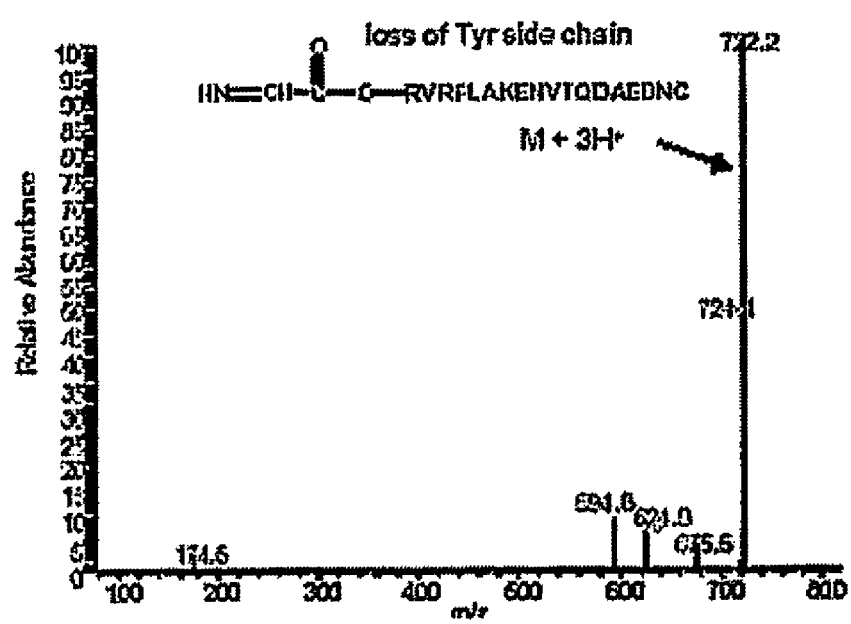
FIG. 5 is a CID Spectrum of an N-Terminal modified peptide of the present invention.

CID spectra of the modified amino acids Gly, Ala, Val, Leu, Glu, Asp, His, Met, Phe, Ser, and Trp produces an ion with m/z=94 (m/z=108 for Glu diethyl ester) corresponding to loss of the side chain and formation of an imine (FIG. 4). Similarly, side chain loss is seen in CID spectra of modified peptides (FIG. 5). The best reaction conditions to favor N-terminus modification over lysine residues (determined by LC/MS) are pH5.5 (1:1 0.1M propionate or 0.01M acetate buffer and acetonitrile, reagent with R"=m-$NO_2$ and incubation at 37° C. for 1 hour. Varying the tube lens voltage in Q1 allows for observation of the imine on two of the modified peptides, which was then selected for CID. The spectra produces a mass shift of the b-ions in reference to the unmodified peptides, which corresponded to the mass of the N-terminal side chain.

In this regard, side loss is observed for a great number of N-terminal modified amino acids and peptides under CID conditions pH 5.5 and reagent with R"=m-$NO_2$ favor N-terminal modification over Lys modification as seen by LC/MS Product ion spectra of the peptide imine resulting from side chain loss exhibit a mass shift in the b-ions which corresponding to the m/z of the side chain.

The table below provides examples of side chain loss of modified amino acids upon CID.

| Amino Acid | (Boc-HN-CH(R)-C(=O)-O-O-) | (H₂N-CH(R)-C(=O)-O-Li) | Neutral loss by CID | Side chain |
|---|---|---|---|---|
| Gly | 212.03 | 96.1 | 1.00 | H— |
| Ala | 226.13 | 110.1 | 15.02 | CH₃— |
| Val | 254.15 | 138.0 | 43.09 | (CH₃)₂CH— |
| Leu | 268.18 | 152.1 | 57.12 | (CH₃)₂CHCH₂— |
| Glu | 325.96 (diethyl ester) | 210.0 | 87.10 | CH₃CH₂OC(=O)(CH₂)₂— |
| Asp | 283.9 (dimethyl ester) | 168.0 | 73.07 | CH₃OC(=O)CH₂— |
| His | 291.9 | 176.1 | 80.94 | (imidazolyl)-CH₂— |
| Met | 285.9 | 170.1 | 75.14 | CH₃S(CH₂)₂— |
| Phe | 302.01 | 186.0 | 91.13 | (phenyl)-CH₂— |
| Ser | 242.0 | 126.0 | 31.06 | HOCH₂— |
| Tyr | 318.0 | 202.1 | 107.13 | HO-(phenyl)-CH₂— |
| Trp | 341.01 | 225.0 | 132.0 | (indolyl)-CH₂— |

The invention thus being described, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

REFERENCES

Throughout this application, various publications are referenced. All such references, including those listed below, are incorporated herein by reference in their entirety.

Yates, J. R. *J. Mass. Spectrom.* 1998, 33, 1-19.

Aebersold, R.; Goodlett, D. R. *Chem. Rev.* 2001, 101, 269-295.

Glocker, M. O.; Borchers, C.; Fieldler, A.; Suckau, D.; Przybylski, M. *Bioconjugate Chem.* 1994, 5, 583-590.

Bonetto, V.; Bergman, A.; Joernvall, H.; Sillard, R. *Anal. Chem.* 1997, 69, 1315-1319.

Aebersold, R.; Goodlett, D. R. *Chem. Rev.* 2001, 101, 269-295.

McLuckey, S. A.; Reid, G. E. *J. Mass. Spectrom.* 2002, 37, 663-675.

Kelleher, N. L.; Lin, H. Y.; Valaskovic, G. A.; Aaserud, D. J.; Fridriksson, E. K.; McLafferty, F. W. *J. Am. Chem. Soc.* 1999, 121, 806.

Bourgeois, M. J.; Campagnole, M.; Filliatre, C.; Maillard, B.; Manigand, C.; Villenave, J. J. *Tetrahedron* 1982, 38, 3569-3577.

Majetich, G.; Wheless, K. *Tetrahedron* 1995, 51, 7095-7129.

Hawkins, C, L.; Davies, M. J. *Biochem. Biophys. Acta.* 2001, 1504, 196-219.

Griep-Raming, J.; Meyer, S.; Bruhn, T.; Metzger, J. O. *Angew. Chem. Int. Ed. Engl.* 2002, 41, 2738-2742.

Julian, R. R.; May, J. A.; Stoltz, B. M.; Beauchamp, J. L. *Angew. Chem. Int. Ed Engl.* 2003, 42, 1012-1015.

Yin, H.; Hachey, D. L.; Porter, N. A. *J. Am. Soc. Mass Spectrom.* 2001, 12, 449-455.

We claim:

1. A method of identifying protein or peptide sequences, comprising:
    providing a protein or peptide sample;
    providing a peroxycarbonate solution, wherein the peroxycarbonate solution comprises the following peroxycarbonate compound:

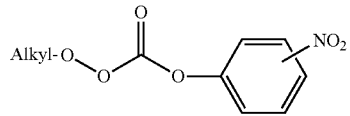

wherein $NO_2$ group is in para- or meta-position;
    combining the protein or peptide sample and the peroxycarbonate solution to perform a reaction between lysine residue amino groups and the peroxycarbonate compound which yields lysine peroxycarbamates;
    performing a mass spectrometric analysis of the lysine peroxycarbamates to obtain the protein or peptide sequence.

2. The method of claim 1, further comprising an incubation step after the combining step.

3. The method of claim 2, wherein the incubation step comprises incubating the sample solution at room temperature.

4. The method of claim 1, wherein the mass spectrometic analysis is a Matrix Assisted Laser Desorption Ionization (MALDI) mass spectrometer.

5. The method of claim 1, wherein the $NO_2$ group is in para-position.

6. The method of claim 1, wherein the $NO_2$ group is in meta-position.

7. The method of claim 1, wherein the mass spectrometric analysis comprises collision induced dissociation (CID).

8. The method of claim 7, wherein mass spectrometric analysis comprises first forming H, Li, Na, K, or Ag peroxycarbamate adducts.

9. The method of claim 1, wherein mass spectrometric analysis follows LC separation of the peroxycarbamate compound.

* * * * *